United States Patent [19]

Cooke et al.

[11] Patent Number: 5,006,050

[45] Date of Patent: Apr. 9, 1991

[54] HIGH ACCURACY DISPOSABLE CASSETTE INFUSION PUMP

[75] Inventors: James E. Cooke, 1506 Madruno Ave., Palo Alto, Calif. 94306; Philip Barkan, Stanford; Gregory Kovacs, Palo Alto, both of Calif.

[73] Assignee: James E. Cooke, Tampa, Fla.

[21] Appl. No.: 283,107

[22] Filed: Dec. 9, 1988

[51] Int. Cl.⁵ ............................................. F04B 43/04
[52] U.S. Cl. .................................. 417/478; 604/153; 417/479
[58] Field of Search ................. 417/478, 479; 604/141, 604/151, 153

[56] References Cited

U.S. PATENT DOCUMENTS

| | | | |
|---|---|---|---|
| 4,303,376 | 12/1981 | Siekmann | 417/395 |
| 4,453,931 | 6/1984 | Pastrone | 604/153 |
| 4,657,490 | 4/1987 | Abbott | 417/479 |
| 4,818,186 | 4/1989 | Pastrone et al. | 604/153 X |

Primary Examiner—Leonard E. Smith
Attorney, Agent, or Firm—Townsend and Townsend

[57] ABSTRACT

An infusion pump for delivery of drugs to a patient includes a unit in which the pump mechanism is situated and a cassette through which the drugs to be delivered to the patient are pumped. The cassette includes a path for the fluid to flow from a drug vial to an outlet port. Disposed along the path are recesses for an inlet valve, a pressurization region, and an outlet valve. The cassette is sealed by an elastomeric layer to maintain the drugs to be delivered in a contaminant-free condition. The pump includes an inlet valve which has a contour matching the recess of the inlet port, and an outlet valve matching the recess of the outlet port. By biasing the inlet and outlet valves against the recesses, a pumping chamber is created. A piston in the unit pressurizes the pumping chamber to open the outlet valve and permit fluid to escape. By appropriate timing of the operation of the inlet valve and the piston, a continuous stream of fluid is delivered by the pump to the patient.

15 Claims, 5 Drawing Sheets

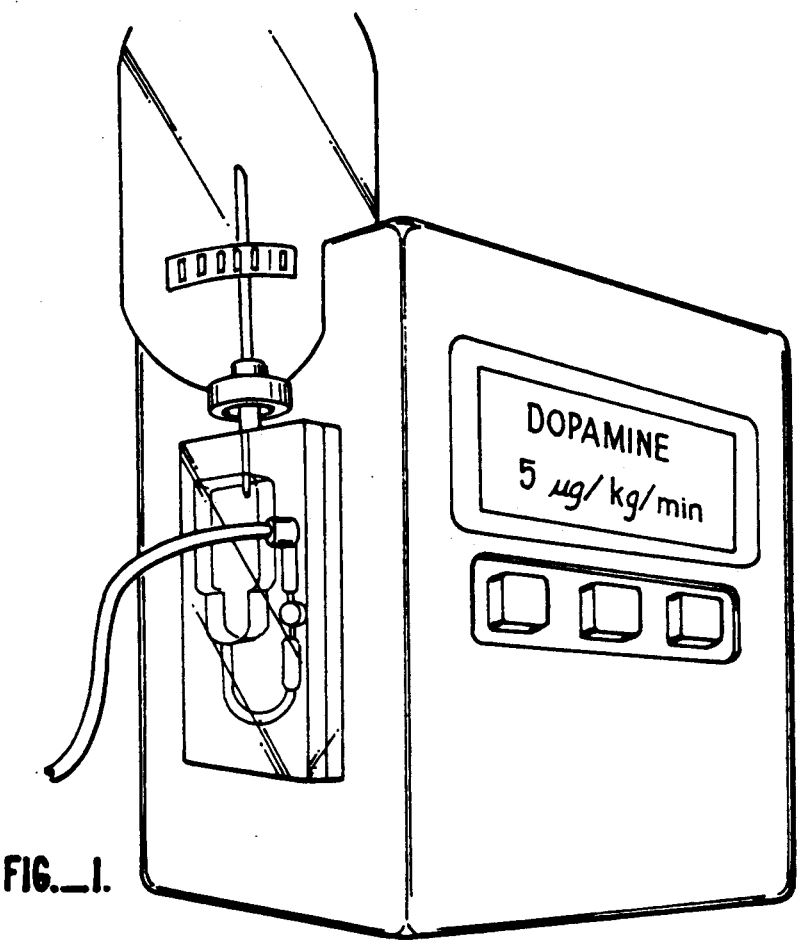
FIG._1.
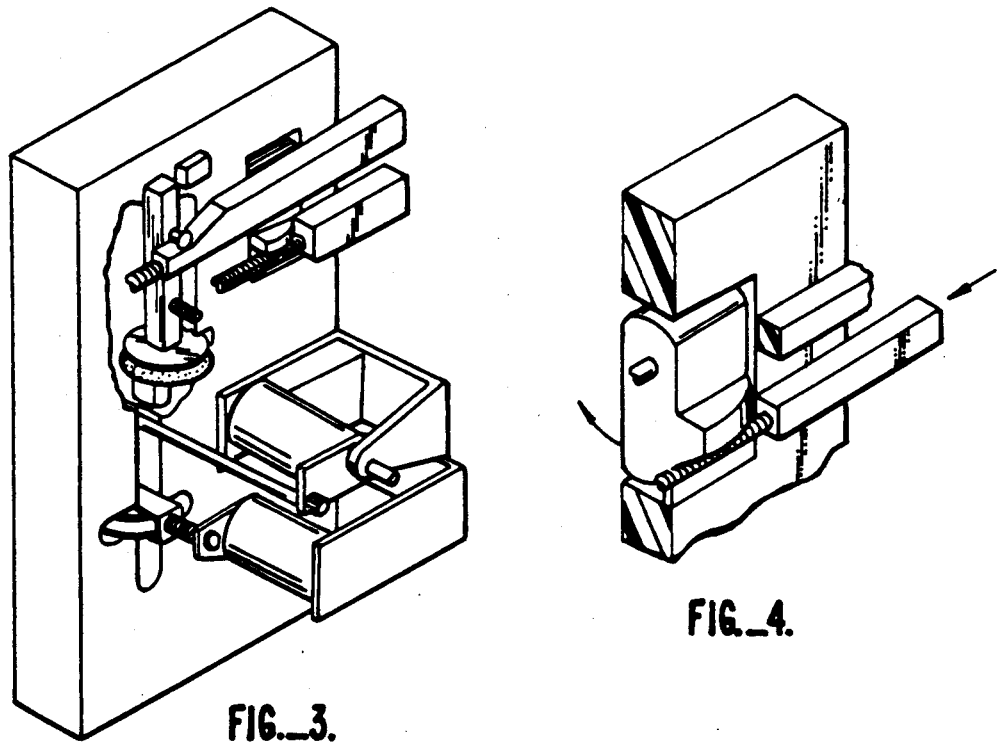
FIG._3.
FIG._4.

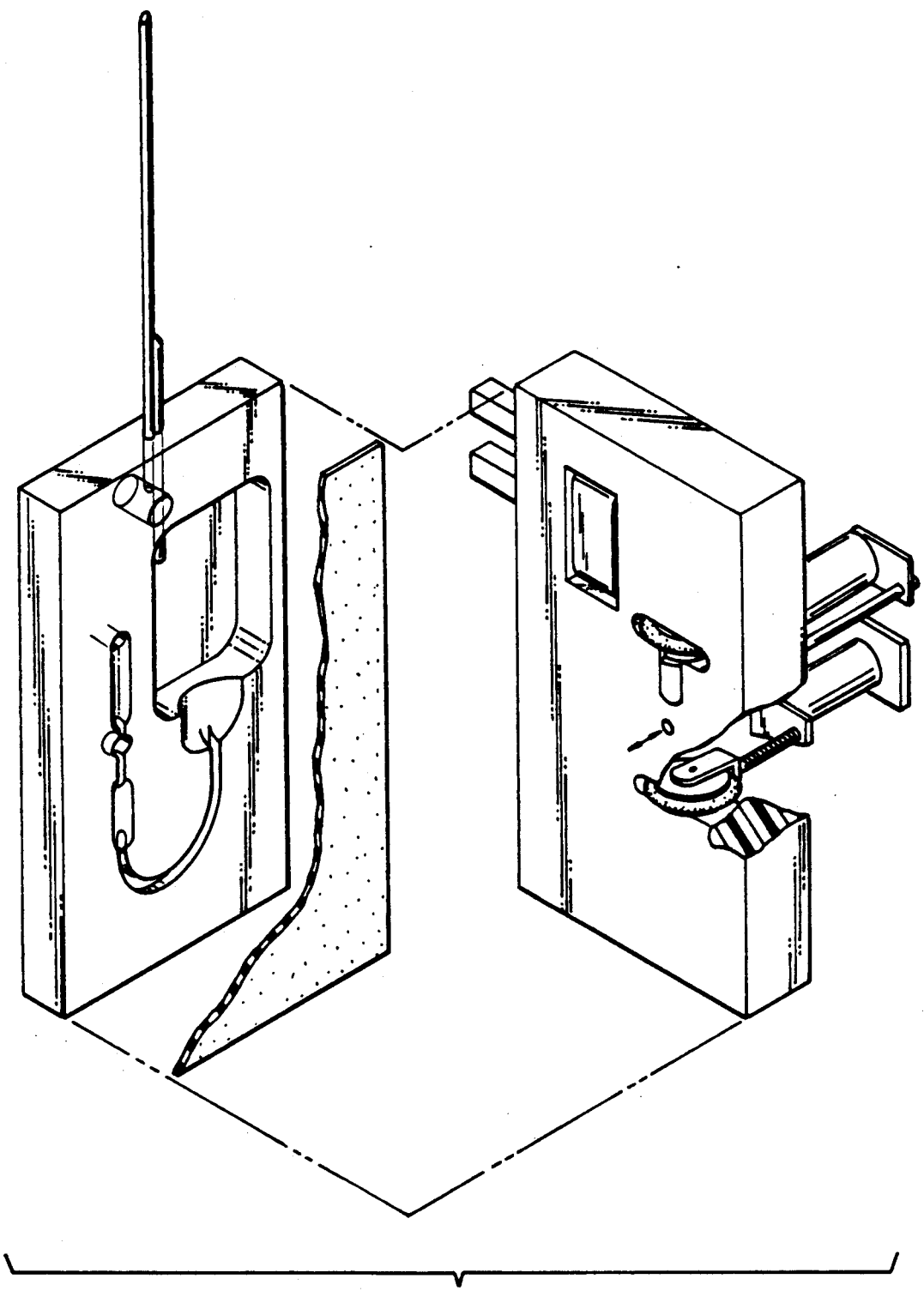
FIG._2.

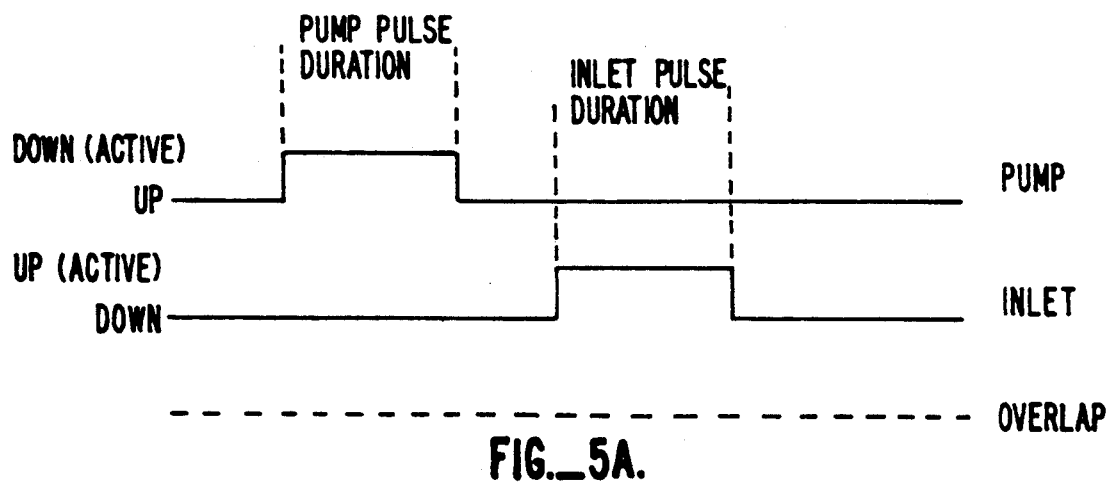
FIG._5A.
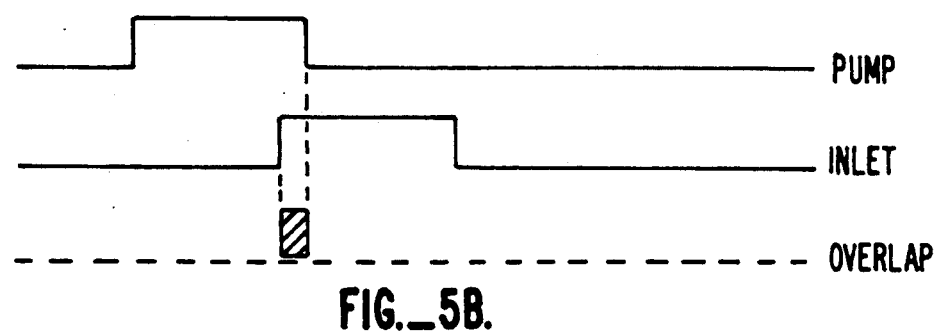
FIG._5B.
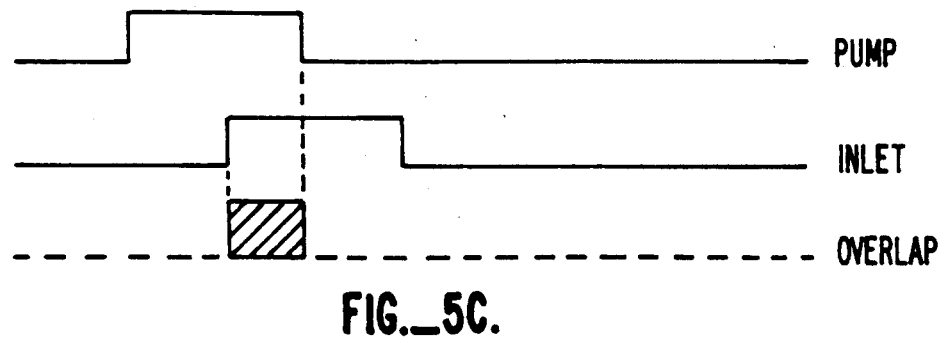
FIG._5C.

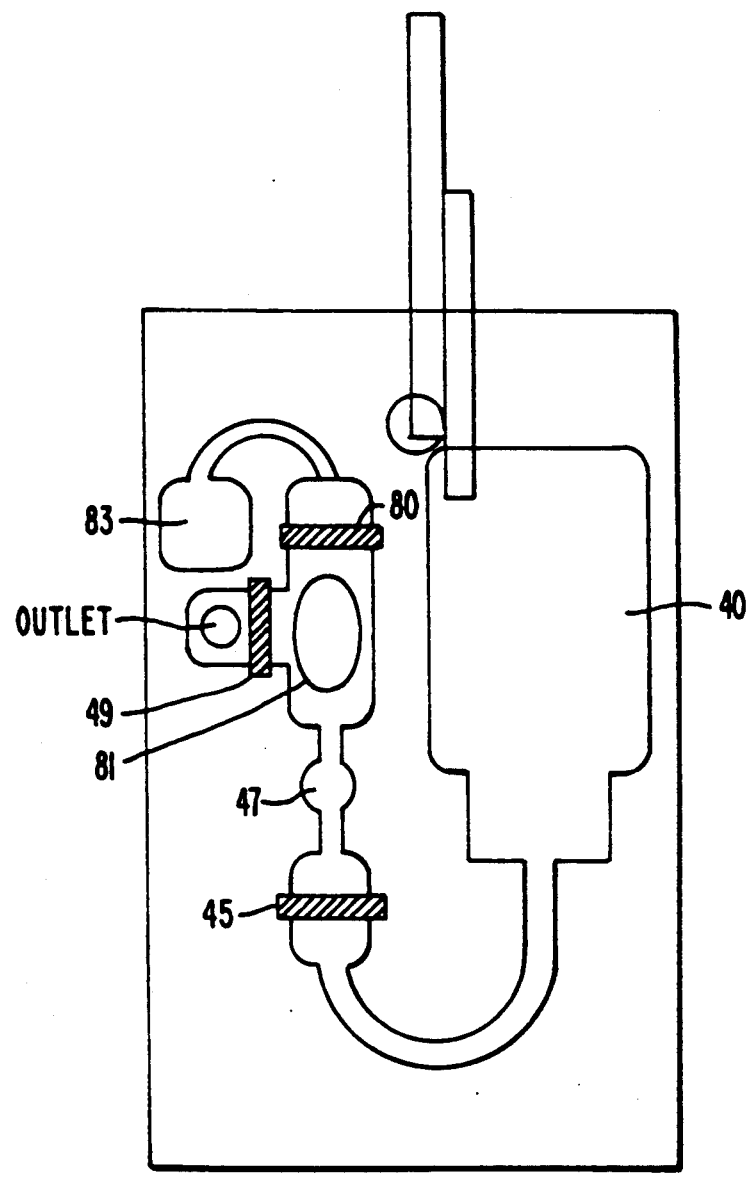
FIG._6.

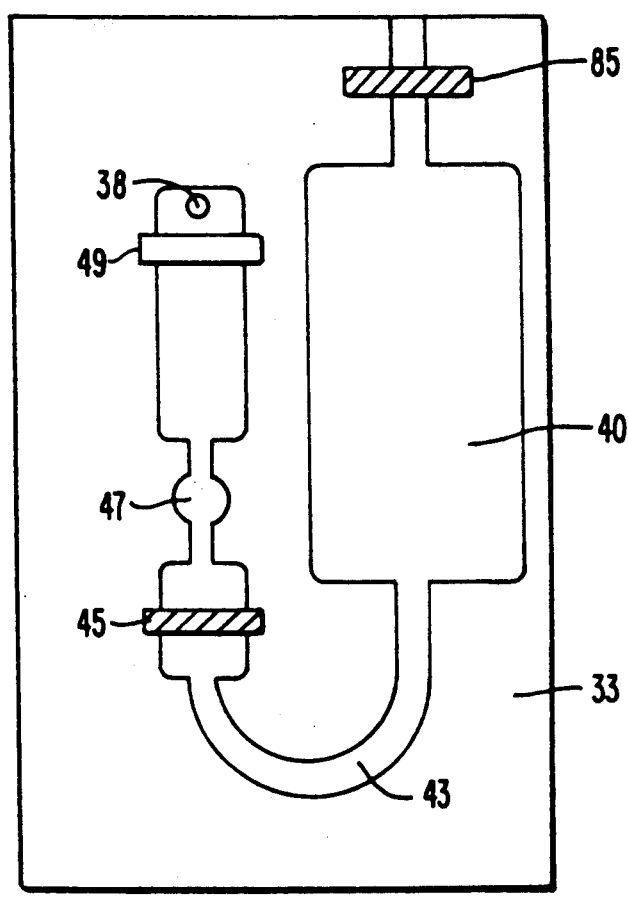
FIG._7.

HIGH ACCURACY DISPOSABLE CASSETTE INFUSION PUMP

BACKGROUND OF THE INVENTION

1. Field of the Invention

This invention relates to intravenous infusion pumps, and in particular, to a high accuracy infusion pump for the delivery of drugs to patients and in which the liquid delivered is pumped through a disposable cassette.

2. Description of the Prior Art

In the operating rooms of hospitals, most of the interventions and maneuvers which anesthesiologists perform involve potent and dangerous drugs. From an anesthesiologist's point of view, the goal in any procedure carried out in an operating room is to take an awake patient and using specialized drugs and techniques make him unconscious and unresponsive so that surgery can safely performed. In planning anesthetic treatment, the anesthesiologist considers the drugs and techniques used, how these drugs alter the patient's physiology, the nature of the surgery, and concurrent medical illnesses unrelated to the surgery. For example, consider a patient who has had an intracerebral hemorrhage, and is scheduled for surgery to control an aneurism of one of the major blood vessels in the head. Concurrent medical conditions might include hypertension, hypovolemia (low blood volume), and increased intracranial pressure. Dangers related to the surgery include a risk of uncontrollable hemorrhage, very long surgery, the potential of air entering the blood stream and occluding blood flow to the lungs, heart, brain, or other organs, as well as cerebral edema or excess brain swelling.

The anesthesiologist administering the anesthetic for such a patient typically will use up to eight different drugs to safely induce the desired state of unconsciousness in the patient. At the same time, other drugs, often as many as ten, are used to keep the patient asleep and immobile for the duration of the surgery. Some of these drugs will be applied continuously. Using specialized monitors, the anesthesiologist will watch the effects of the interventions and titrate the doses of these drugs. As the anesthesiologist adjusts the medications that keep the patient asleep, he or she must also watch for changes caused by the surgery. During the hypothetical surgery described, the anesthesiologist will be called on to drastically reduce the blood pressure of the patient for up to 30 minutes to enable the surgeon to clip the fragile aneurism. The resulting hypotension can be difficult to control, and the drugs used to cause it must be adjusted as frequently as every two or three minutes. At the end of the procedure, the anesthesiologist must then awaken the patient, restore his breathing, continue to carefully control blood pressure, reverse the effects of the anesthetics and transport the patient to a suitable care unit.

There are now several different techniques for anesthesiologists to apply drugs to patients. Probably the most common method is to give the drugs intravenously as a bolus, in other words, doses of several milliliters at a time. Continuous infusions, in which very small quantities of drugs are delivered continuously to a patient over an extended period of time, are another common method of administering drugs. Many of the newer drugs and techniques, require drugs to be given as continuous infusions which are precisely metered. In the example just discussed, one of the drugs used for manipulation of blood pressure might be nitroprusside. The infusion rate for this potent drug must be carefully adjusted every few minutes based upon the patient's response.

There are presently two types of continuous infusion systems. The first is a gravity-dependent bag-and-tubing setup with flow controlled by a variable orifice. The alternative is an electrically-powered infusion pump having an external drug reservoir. Unfortunately, all of the systems developed to date have at least one of many disadvantages. For example, size is a major constraint upon equipment designed for an operating room. Because the anesthesiologist must attend to both the equipment and the patient, the equipment must be within arm's reach. Unfortunately, operating rooms are already overcrowded with carts, monitors, wires, tubing, blood warmers, humidifiers, and the like. There may also be significant special constraints caused by surgical equipment employed as well as by the layout of the room. Most infusion pumps now commercially available are much too large to be used efficiently in an operating room.

Present systems also involve a tangle of tubes, wires, hoses, and the like, which frequently encircle each other forming dangerous knots. If the intravenous lines from potent drug infusions become entangled, the wrong amount or the wrong drug might be delivered to the patient. The tangle also increases the chance of a disconnection, and becomes particularly dangerous when the patient is moved from the operating room table to the patient's bed, as well as when the patient or the table are moved during the course of an operation. Most existing infusion pumps require a power cord and two intravenous "IV" lines—one from the IV bag drug reservoir to the pump and one from the pump to the patient.

Another disadvantage of conventional systems is the time required to set them up before use. The setup procedure includes opening the drug vial, opening a syringe, drawing the drug into the syringe, opening a bag for diluting the drug, injecting the drug into the bag, inserting an IV tube set into the bag, labeling the bag, and then purging air from the tubing. The infusion pump must also be plugged in and the IV tubing connected to the pump mechanism to supply the drug.

Prior art continuous infusion pumps are also expensive. Because of the need for sterility, multiple disposable parts are required for each infusion. For example, a new drug vial, syringe and needle, IV bag, tubing set, and appropriate pump parts are required. Each part has an expense which is incurred during setup, even if the pump is not needed during the procedure.

Another disadvantage of prior art infusion pumps is that the infusion rate is susceptible to change due to temperature, table height, back pressure, partial occlusion, bag height, and the relative height and rates of other infusions going into the same IV line. (In most cases, several infusions will be "piggy-backed" into one IV line.) All of these systems require that the anesthesiologist verify the infusion rate frequently and make adjustments. While infusion pumps are less sensitive to these effects than other systems, corrections may still be required.

A further disadvantage of the prior art systems is their potential for error. Because all drugs look the same once they leave the vial, errors include mislabeling of the IV bag and calculation errors. The calculation errors can occur because drugs are delivered in various concentrations and usually adjusted by patient weight. For example, nitroprusside, discussed above, is supplied in vials. After dilution it is often delivered at a rate of 1 microgram per kilogram of body weight per minute. The anesthesiologist must determine the correct conversion, and this calculation must usually be made under stressful circumstances.

SUMMARY OF THE INVENTION

We have developed a new infusion pump based system for administering continuous infusions of potent drugs, which system is particularly suited for use in operating rooms. The system of our invention is compact, battery powered, and automatically performs the necessary conversions for dosage calculations. The pump is able to read the label of the drug container to greatly reduce labeling and calculation errors. Because of its small size and battery operation, the pump may be readily employed in intensive care after surgical procedures by simply transporting the pump with the patient to the intensive care unit. The small size, absence of power cords, and decreased chance of calculation errors make the system particularly suitable for patients being managed with multiple drug infusions. The pump may also be efficiently used for maintaining continuous infusions of potent drugs during transport of the patient, whether by ambulance, helicopter, or otherwise. The system substantially minimizes the tangling problem of prior art systems. Furthermore, by employing linear actuators, it consumes very little power, enabling extended operation off a small battery pack, which can be recharged as necessary.

In a preferred embodiment of our invention, a pump for supplying a controlled quantity of fluid includes a cassette means for defining a fluid path, the cassette means including an inlet port for receiving the fluid, an outlet port for supplying the fluid, and a pressurization region for forcing the fluid out of the outlet port. The cassette means is sealed by a flexible membrane being disposed over it to enclose the fluid path and separate the fluid path from the pump. An inlet valve is disposed in proximity to the flexible membrane and the inlet port. The inlet valve opens and closes the inlet port. A controllable piston is disposed in proximity to the flexible membrane in the pressurization region for forcing fluid out of the outlet port. Typically, the outlet valve consists of a spring-loaded member having a region shaped to match the outlet port, with the spring-loaded member biasing the outlet port closed in the absence of sufficient pressure to overcome the spring.

The pump acts on the cassette by means of an inlet valve, a piston, and an outlet valve. The fluid is pumped in only one direction because the outlet valve is a normally closed valve which is opened in response to fluid pressure. In one method of operation, after fluid is introduced into the cassette, the inlet valve is closed. As the piston increases the pressure in the pressurization region, the output valve is forced open and the fluid escapes. When the pressure drops sufficiently, the outlet valve closes, and the inlet valve is opened to admit more fluid. The pressure-activated outlet valve is suitable for monitoring or measuring the activity and accuracy of the pump. The preferred method is to measure the movement of the valve very accurately, and with electronic feedback control, use that movement to measure the volume of fluid pumped. The timing of the inlet valve and pump actuators thus can be precisely adjusted to provide accurate fluid flow. The outlet valve deflection information, available through a transducer, provides information which is substantially representative of the operational state of the pump, thereby enabling control of the timing. In addition to control of timing, the outlet valve allows detection of occlusion or partial occlusion of inflow to or outflow from the pump, gas trapped in the pump, mechanical failure, disconnection of the line to the patient, and exhaustion of fluid supply.

BRIEF DESCRIPTION OF THE DRAWINGS

FIG. 1 is an exterior view of a preferred embodiment of the infusion pump.

FIG. 2 is an exploded perspective view of the base of the infusion pump showing its coupling to a cassette.

FIG. 3 is a perspective view of the upper side of the pump illustrating the solenoids driving the inlet valve and piston.

FIG. 4 is a perspective view illustrating the apparatus for purging air from the fluid reservoir.

FIGS. 5a–5c are timing diagrams illustrating the operation of the pump piston and inlet valve.

FIG. 6 is a side view of another embodiment of the cassette, with a special air bleeding section.

FIG. 7 is a side view of another embodiment of the cassette with an extra inlet valve.

DETAILED DESCRIPTION OF THE PREFERRED EMBODIMENTS

FIG. 1 is a perspective view of the exterior of a preferred embodiment of the infusion pump system of our invention. Generally, the pump system includes a pumping unit 10, a drug vial 12 containing the drug to be pumped, and a disposable cassette 15 through which the drug is pumped. The exterior of the pumping unit 10 and the drug vial 12 are discussed here; the pumping action and cassette are discussed further below. Throughout this discussion, components appearing in more than one figure have been given the same reference numeral in each figure.

In FIG. 1 the pump includes an exterior case 16, a display area 18, and a desired number of keys 20 and a dial 22 for entry of information to control the pump, and selection of a display format for display 18. Of course, as many keys, dials or other input devices as desired can be provided. In the preferred embodiment, keys 20 will be pushbuttons and display 18 will be a liquid crystal display. The drug vial 12 is maintained in position by a recessed area 21 in the upper left portion of case 16. Cassette 15 is temporarily affixed to the pumping unit 10 by means of a plate 23 on the exterior case 16. Plate 23 will typically have well known pins, protrusions or recesses therein so that the cassette 15 may "snap" in place or otherwise be temporarily, but securely, affixed to the plate 23. The drug container 12 is affixed to the cassette by two hollow bore needles 25, 26 which pierce a rubber seal 30 at the top of the bottle after it is inverted. Needle 25 communicates to ambient air via an opening 39 in cassette 15 to allow air to replace the fluid drawn from the bottle by needle 26.

FIG. 2 is an exploded perspective view showing how the base plate 23 and cassette 15 couple together to enable operation of the pump to transport fluid through the cassette. As shown in FIG. 2, the cassette includes a body portion 32 within which a series of recesses and openings have been formed in a front surface 33. The back surface 35 has no openings from which fluid may escape except for an outlet 38 and an opening 39 connecting air inlet 25 to ambient.

The recesses formed in cassette body 32 include an inlet reservoir 40 which communicates with the drug vial via needle 26. A channel 43 extends between the inlet reservoir 40 and the recesses defining an inlet port 45, a pressurization region 47, and an outlet port 49. Once fluid reaches outlet port 49, it passes through opening 38 and out of the pump into tubing which ultimately supplies the drug to the patient. While a continuous recess of varying depth and cross-sectional profile has been shown in FIG. 2, other techniques may be employed to provide the fluid path. For example, the channel and other portions of the fluid path could be formed entirely within the body 32 as opposed to at its front surface 33.

A flexible elastomeric membrane 50 affixed to interior surface 33 of cassette body 32 completely seals the cassette from the pump mechanism, thereby maintaining the drug to be delivered in a contaminant-free condition. Membrane 50 is attached securely to the cassette body 32 using a suitable adhesive or other mechanical means. In the preferred embodiment a single membrane is employed to seal all of the recesses. In other embodiments, for example, where the recess is not continuous, separate membranes having different compliances, if desired, could be employed.

It should be understood that the elastic membrane need not be truly elastic, but rather only flexible. For example, a thin membrane of polycarbonate, metal, or silicon could be employed. Flexibility in such cases can be achieved by either making the membrane very thin or by forcing the membrane to flex at certain places on the membrane, for example, by scoring lines on the surface or molding in lines. The resulting thin areas are the locations at which the membrane flexes.

In a further embodiment, the membrane surface is scored at several places and prestressed before being attached to the cassette. By creating sections of the membrane that preferentially buckle up or down out of the plane of the membrane, the cassette can be constructed such that the membrane "flip-flops" between two preferred states. The normal state of the section could be up, until a small force is applied to cause it to flex down. The membrane then remains in the down position until the force is released to allow the membrane to abruptly flex to the up position.

Furthermore, the membrane need not be flat. In some embodiments it will consist of a molded piece with preformed areas which are thicker and designed to partially fill the channel formed between the membrane and the hard cassette. By constructing these in a manner to reduce the force required to seal the channel, sensitivity of the pump to variables such as inlet and outlet fluid pressure is reduced.

The pump mechanism which acts upon the membrane is shown in FIGS. 2 and 3. FIG. 2 shows the pump mechanism from the cassette side of base plate 23, while FIG. 3 shows the mechanism from the interior side. As shown in FIG. 2, there typically will be four openings in base plate 23. In other embodiments additional openings for additional valves and pressure sensors may be provided. A first opening 52 allows the inlet valve 58 to extend through the base plate, while the second opening 53 is provided for the piston 61. A third opening 54 is provided for the outlet valve 65 and pressure sensing foot 70, while the fourth opening 55 allows a mechanism to protrude through for flushing air from the system when it is first affixed to a drug supply.

The pump mechanism includes an inlet valve 58 driven by a first solenoid 60 and a pressurization piston 61 driven by a second solenoid 63. The outlet valve 65 is supported on a cantilever 66 and biased closed by means of spring 68, or other suitable means. A foot 70, coupled to the outlet valve, allows measurement of outlet pressure. Although the actuators have been described as solenoids, cams on a rotating shaft, piezoelectric devices, electrostatic actuators, or stepping motors operating through gears may also be employed. Nonrotary systems generally are preferred because of their lower frictional losses of power.

The operation of the pump is based upon the motion of the inlet and outlet valves. The inlet and outlet valves have an exterior contour which corresponds to the interior contour of the inlet 45 and outlet 49 ports. Thus, when the inlet valve 58 is closed, its periphery compresses the elastomeric layer 50 downward against the interior surface of the recess defining the inlet port 45, thereby preventing further fluid flow from reservoir 40 into region 47. In a similar manner, when the outlet valve 65 is closed, its periphery compresses elastomeric layer 50 against the internal surface of outlet port 49, thereby preventing flow through the cassette. The fluid path is pressurized by means of piston 61 which operates through opening 53 to compress membrane 50 into pressurization region 47.

In operation, initially both the inlet valve 58 and the outlet valve 65 are pushed against membrane 50 causing the channel to be sealed at these two places and forming a pumping chamber. The pumping chamber is defined by the membrane 50 and the channel machined into the cassette body 32. The ends of the chamber are defined by the regions where the valves press the membrane against the channel bottom. Once the channel is closed, the chamber is pressurized by solenoid 63 driving piston 61 against the membrane. The piston presses the membrane in, attempting to compress the fluid in the chamber and thereby increasing the pressure of the fluid. When the pressure is sufficient, the fluid acts on the foot 70 connected to outlet valve 65 to lift the outlet valve a small amount off the bottom of the channel, thereby allowing a fluid to escape from the pumping chamber. Fluid will continue to flow under the outlet valve 65 until the pressure in the chamber falls enough to allow the outlet valve to again seal. Then the piston is retracted. Next, the inlet valve 58 is retracted, allowing fluid from reservoir 40 to refill the pumping chamber. Solenoid 60 then closes the inlet valve 58, and the cycle is repeated with the piston 61 pressurizing the chamber to cause fluid to flow beneath outlet valve 65. Of course, by varying the timing of the inlet valve operation and the rate or throw of piston 61 (see FIGS. 5a-5c), the flow rate of the pump can be varied. Typically, enough volume will be released from the pumping chamber to allow the outlet valve to close before the next piston cycle. Thus, in operation, the outlet valve will usually close at least once a cycle so that a pulsating stream of fluid passes through the pump.

The pump can also be operated using a different order of steps. For example, the piston could be retracted or the inlet valve lifted before the outlet valve has closed. Either action depressurizes the pumping chamber, allowing the outlet valve to close before the maximal pulse volume has been pumped. Thus, additional means are provided for controlling the flow rate. In addition, by careful control of only the piston, the pump may be operated with a passive inlet valve, i.e., one which is not driven by its own solenoid but instead allows fluid to enter the pumping chamber passively to be forced out by the piston.

While the pump is operating, the pressure-sensing foot 70 bears against the membrane 50 and thereby provides information about the pressure of the fluid within the cassette 32. This information is detected by sensing the position of the cantilever beam 66 to which the foot is affixed. In this manner information is given about the pressure in the chamber, enabling accurate measurement of the drug supplied through the cassette. Furthermore, this portion of the system can be used to determine whether or not an error condition exists, such as air in the pump or occlusion of the inlet or outlet ports. In the preferred embodiment, the primary source of information is movement of the outlet valve, which is sensed by a small sensor 69 operating on a Hall effect to detect the position of magnet 67. Of course, piezoelectric techniques, a moving coil, or other techniques also may be employed. Furthermore, instead of using a single pressure-sensing foot, very small silicon-based solid state pressure sensors could be employed in one or more chambers to allow for more accurate sensing of the operation of the pump.

After installation of a drug vial in the pump unit, it is necessary to pump a quantity of fluid from the drug vial 12 through the system to prevent the inadvertent injection of air into the patient. This is the function of the apparatus shown in further detail in FIG. 4. As shown there a rotatable member 71 is suspended from a pin 72. Member 71 includes a curved surface 73 against which another slidable member 75 will be forced. Spring 77 causes member 75 to return to its position as shown in, FIG. 4 after each depression. When member 75 is depressed, it bears against surface 73 causing member 71 to rotate about axis 72. Rotation of member 71 compresses the elastomeric material 50 over reservoir 40, thereby enabling manual pumping of air from the system when it is first charged with fluid. While this aspect of the system is shown as manually operable, it should be appreciated that it could also be performed electrically by using another solenoid to drive the member 75, or member 73, thus eliminating the need for member 75.

The quantity of fluid pumped is a complex function of fluid viscosity, pump membrane mechanical properties, pumping force, pump timing and other parameters. FIGS. 5a-5c are timing diaphragms illustrating how, if other parameters are held constant, pump timing can be used to control fluid flow. As shown in FIG. 5, pump timing includes the durations of the pump piston and inlet valve activations, as well as the relative phase between activations of the piston and inlet valve. FIGS. 5a-5c illustrate how the flow rate or bolus size can be changed by adjusting the relative overlap or phase between the inlet valve and pump piston activations. Within certain limits increasing the pump and/or inlet pulse widths will increase the bolus size or flow rate, and likewise, decreasing the pump and/or inlet pulse width will decrease flow rate. The control of flow rate is thus achieved by suitable variations of any or all of pump pulse width, inlet pulse width, and the overlap of those pulses.

FIG. 5a is a timing diagram illustrating the relationship of a pump piston pulse to an inlet valve pulse. As shown in FIG. 5a, for this circumstance there is no overlap of the two pulses.

In FIG. 5b the timing of the pump pulse and the inlet valve pulse are adjusted to overlap. The result will be a decrease in the quantity of fluid pumped with respect to the timing shown in FIG. 5a. In FIG. 5c the overlap is increased still further, resulting in a further decrease in fluid pumped. The outlet valve deflection information, available through a transducer, provides information which is substantially representative of the operational state of the pump, thereby enabling control of the timing. In addition to control of timing, the outlet valve allows detection of occlusion or partial occlusion of inflow to or outflow from the pump, gas trapped in the pump, mechanical failure, disconnection of the line to the patient, and exhaustion of fluid supply.

In a preferred embodiment of the invention, the drug vial is automatically identified by the pumping system. By placing a bar code label 28 on the outside of the vial, a conventional bar code reader disposed inside the pump housing may read the encoded information. The encoded information may include drug type, viscosity, concentration, expiration date, interations with other drugs, or the like. By utilizing this information a microcomputer situated inside the pump housing can, under well known program control, calculate appropriate internal control algorithms and dose rates in desired quantities of drug per unit of body weight per unit time. The dial or keys on the front panel can be used to supply the patient's weight enabling the internal computer to calculate and display to the user the dosage rate in the most convenient format. If bar code is employed on the labels, then the vial may be turned slowly to allow the beam to scan the bar code label. Alternatively, well known scanning apparatus may be built into the bar code reader to eliminate the need to rotate the vial. In other embodiments metal contacts are formed on the label of the drug vial, or on the vial itself, to enable electrical detection of its contents. Magnetic media or mechanical contacts may also be used to achieve the same function.

In the preferred embodiment of the cassette, two valve sealing areas are employed, one for each of the inlet and outlet valves. In an alternative embodiment sealing areas are provided for additional valves, for example, as shown in FIG. 6. As shown in FIG. 6, the location of inlet valve seat 45 is the same as FIG. 2. The location of the outlet valve seat 49, however, has been moved to a side channel. An additional sealing area 80 has been added and an additional valve positioned over it, which is normally in the closed position. The pressure sensing foot 70, or other apparatus, is positioned over region 81.

Operation of this embodiment is the same as the embodiment depicted in FIG. 2. In particular, when the valve over area 80 is closed, the inlet valve allows fluid to flow past the seat 45 and into the pumping chamber 47. Once the piston is activated, fluid pressure will act on the outlet valve pressure sensing foot, located over sensing area 81 to open the outlet valve positioned over the outlet valve area 49. Thus, the outlet valve is at right angles to the outlet path in the preferred embodiment. The additional valve area 80 is employed if air enters the pump. In such case, a solenoid connected to the valve over seat 80 opens that valve, while the inlet valve over seat 45 is also opened. This allows fluid to pass in a straight path from the inlet valve area through the pumping piston area, through the area under the outlet valve pressure sensing area 81, and through the valve area 80 to be collected in an extra reservoir 83. The passage of fluid through these areas carries out any air which has collected in the pumping chamber.

In other embodiments of the invention, the cassette portion described above is not disposable. Instead, it is permanently attached to the pump body, thereby enabling the entire pump and cassette mechanism to be much smaller and lighter. The resulting pump is more portable, and may be implantable.

Although in the preferred embodiment a single inlet valve has been described, to further minimize any effect of orientation of the pump with respect to vertical on fluid delivered, an additional inlet valve could be employed.

In a further embodiment of the invention, the pumping system itself may be used as a measuring or metering subsystem in conjunction with a lower precision pressurization system, for example, a large bore syringe or the cassette system illustrated with a further piston. FIG. 7 illustrates such an embodiment. In FIG. 7 the cassette depicted is similar to that shown in FIG. 2, and corresponding reference numerals have been employed. In the cassette of FIG. 7, however, the volume of chamber 40 has been expanded, and another inlet valve 85 added.

To operate the pump with this cassette, inlet valve 85 is first opened and the chamber 40 filled with fluid. Then the inlet valve 85 is closed, and chamber 40 compressed using a crude piston or foot. Next inlet valve 45 is opened. If the pressure from chamber 40 is great enough, the outlet valve 49 will open. Its motion will be sensed and modulated by closing inlet area 45.

The pump cassette shown, although requiring an additional actuator, requires fewer solenoid actuator steps. The large volume 40 and associated piston replace the piston bearing on region 47 as the pressurizing means, enabling the pressure to be maintained with fewer, but larger strokes. This system with an extra inlet valve also desensitizes the infusion pump to any effect of change of head in the drug vial. Of course, the piston acting on the smaller pumping region 47 is not necessarily eliminated. It could be employed to increase the accuracy of the pump, if necessary.

The system of this invention described has many advantages over prior art infusion pumps. For example, by employing linear actuators it consumes very little power, enabling extended operation off a small battery pack, which can be recharged as necessary. While the system has been described in several embodiments with respect to specific features and construction, it should be appreciated that such details were for illustration and explanation. The scope of the invention is set forth in the appended claims.

We claim:

1. A pump for supplying a controlled quantity of liquid comprising:

cassette means for defining a liquid path, the cassette means including an inlet region for receiving the liquid, an outlet region for discharging the liquid, and a pressurization region for forcing the liquid from the outlet region;

flexible membrane means disposed over the cassette means to enclose the liquid path;

controllable piston means disposed to move the flexible membrane means to pressurize the liquid in the pressurization region, thus forcing liquid from the outlet region;

inlet valve means disposed in proximity to the flexible membrane means and the inlet region for controlling liquid flow through the inlet region, the inlet valve means capable of operating independently of the controllable piston means;

outlet valve means disposed in proximity to the flexible membrane means and the outlet region for maintaining the outlet region closed except when liquid is being forced from the outlet region;

a second outlet region for discharging any gas in the cassette means, the second outlet region being disposed in the liquid path before the outlet region; and additional outlet valve means disposed in proximity to the second outlet region for controlling gas flow through the second outlet region.

2. A pump as in claim 1 further comprising pressure sensor means for sensing pressure of the liquid in the pressurization region.

3. A pump as in claim 2 wherein the pressure sensing means comprises:

a contact surface disposed to contact the flexible membrane means; and position sensing means for sensing position of the contact surface.

4. A pump as in claim 1 wherein the cassette means comprises a cassette having a rigid body with a first valve seat for the inlet region, a second valve seat for the outlet region, and a recess for the liquid path.

5. A pump as in claim 4 wherein the flexible membrane means comprises an elastomeric membrane affixed to the cassette.

6. A pump as in claim 4 wherein the inlet valve means comprises:

a first member located on an opposite side of the flexible membrane means from the first valve seat and having a contour corresponding to the first valve seat; and inlet valve actuator means for moving the first member between an open position and a closed position.

7. A pump as in claim 1 wherein the outlet valve means comprises:

a second member located on an opposite site of the flexible membrane means from the second valve seat and having a contour corresponding to the second valve seat; and biasing means for biasing the outlet valve closed against the second valve seat.

8. A pump as in claim 7 wherein the biasing means comprises a spring.

9. A pump as in claim 8 wherein the second member is coupled to a cantilever beam, and the spring biases the second member against the flexible membrane means.

10. A pump as in claim 1 wherein the cassette further comprises:

a reservoir for holding a quantity of liquid, the reservoir having an outlet liquid path connected to the inlet region and having an inlet liquid path in which a second inlet region is disposed to receive the liquid.

11. A pump as in claim 10 further comprising second inlet valve means disposed in proximity to the flexible membrane means to control liquid flow through the second inlet region.

12. A pump as in claim 1 wherein the pressurization region is disposed between the inlet region and the outlet region.

13. A pump as in claim 12 wherein the controllable piston means comprises a movable piston aligned to compress the flexible membrane means over the pressurization region.

14. A pump as in claim 13 wherein the piston is electrically actuated.

15. A pump as in claim 14 wherein the piston is moved by a solenoid.

* * * * *